Figure 1:
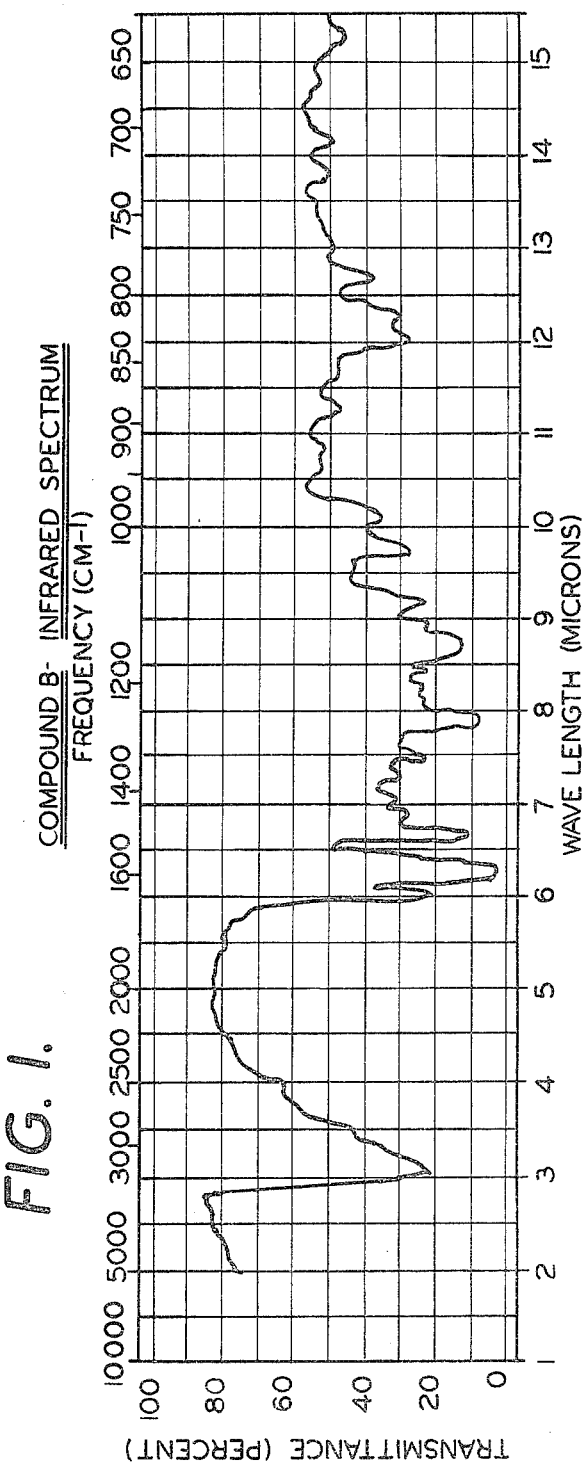

United States Patent [19]

Madaus et al.

[11] 4,168,318

[45] Sep. 18, 1979

[54] 1-(2,4,6-TRIHYDROXYPHENYL)-PROPANEDIONE-(1,2)-COMPOUNDS AND THERAPEUTIC COMPOSITIONS

[75] Inventors: Rolf Madaus, Cologne-Brück; Günter Halbach, Cologne; Wilfried Trost, Bensberg-Frankenforst, all of Fed. Rep. of Germany

[73] Assignee: Dr. Madaus & Co., Cologne, Fed. Rep. of Germany

[21] Appl. No.: 793,113

[22] Filed: May 2, 1977

Related U.S. Application Data

[63] Continuation of Ser. No. 587,450, Jun. 16, 1975, abandoned.

[30] Foreign Application Priority Data

Jun. 14, 1974 [DE] Fed. Rep. of Germany ....... 2428680

[51] Int. Cl.$^2$ ................... A61K 31/34; A61K 31/335;
  C07D 319/14; C07D 307/77
[52] U.S. Cl. ............................. 424/278; 260/340.3;
  260/346.22; 424/285; 542/439
[58] Field of Search ............................. 424/278, 285;
  260/340.3, 346.22 M

[56] References Cited
U.S. PATENT DOCUMENTS

| | | | |
|---|---|---|---|
| 3,117,978 | 1/1964 | Biel et al. | 424/278 |
| 3,158,622 | 11/1964 | Bovet et al. | 424/278 |
| 3,484,448 | 12/1969 | Kramer et al. | 424/278 |
| 3,755,367 | 8/1973 | Green et al. | 424/278 |

OTHER PUBLICATIONS

Madaus et al., Chem. Abst., 82-103142v (1975).

*Primary Examiner*—Stanley J. Friedman
*Attorney, Agent, or Firm*—Sprung, Felfe, Horn, Lynch & Kramer

[57] ABSTRACT

New 1-(2',4',6'-trihydroxyphenyl)-propanedione-(1,2)-compounds of the formula

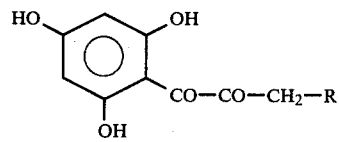

wherein R is

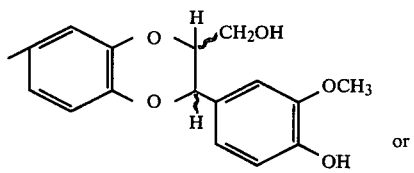

or

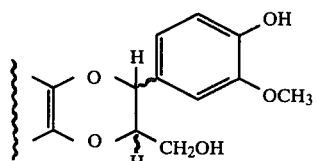

and

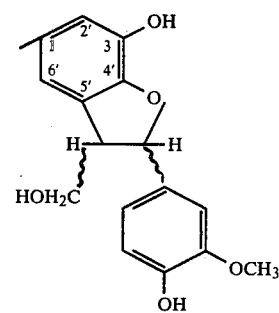

and their acid addition salts are particularly effective in the treatment of liver diseases.

9 Claims, 4 Drawing Figures

COMPOUND B - ULTRAVIOLET SPECTRUM

COMPOUND C - ULTRAVIOLET SPECTRUM

1-(2,4,6-TRIHYDROXYPHENYL)-PROPANEDIONE-(1,2)-COMPOUNDS AND THERAPEUTIC COMPOSITIONS

This is a continuation, of application Ser. No. 587,450, filed June 16, 1975 now abandoned.

The present invention relates to new 1-(2',4',6'-trihydroxyphenyl)-propanedione-(1,2)-compounds, more specifically with such compounds having substitution at the 3-position.

The compounds of the invention are of the formula

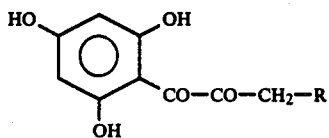

Formula A in which R contains a coniferylalcohol group. The radicals R are isomers of the composition $C_{16}H_{16}O_5$, viz.,

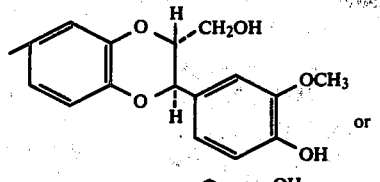

Formula B or

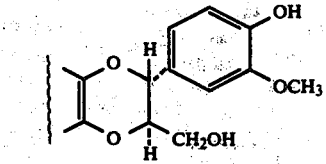

and

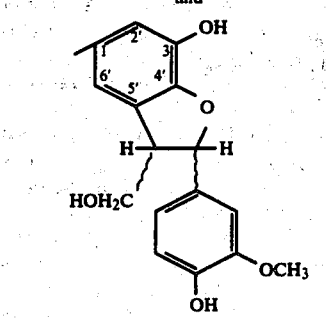

Formula C

The invention also provides, as new compositions the acid addition salts of said compounds and methods for preparing such compounds and salts. Furthermore, the invention provides therapeutic compositions containing such materials, it having been found that these compounds possess a particular effectiveness against liver diseases.

The alkaline γ-pyrone ring opening using simple 3-hydroxyphenyl chromanones by treatment with strong alkalies NaOH, KOH (KOTAKE M. and KUBOTA T., Ann. 543, 253 (1940)) is known. They lead, however, to hydroxy carboxylic acid derivatives (WAWZONEK S./Heterocyclic Compounds, Vol. 2/page 383-385, Ed. R. ELDERFIELD/J. WILEY, New York 1951). If the 3-hydroxyphenyl chromanone compound is treated with a NaOH solution, an autoxidation of about 50% of the initial substance takes place at the same time, and the corresponding dehydro compounds are formed.

The compounds of the invention of the formula A above are produced by the alkaline treatment of coniferyl alcohol substituted with polyhydroxyphenyl-chromanone-3-ols under mild conditions at pH-values of 7.3 to 7.8; 4-6 hour heating, subsequent acidification, drying of the precipitate, extraction of the filtrate with a suitable solvent; distillation of the solvent under reduced pressure and subsequent fractional crystallization of the compound obtained from an appropriate solvent. The coniferyl alcohols, substituted with polyhydroxyphenylchromanone-3-ols which is the reactant for the preparation of the compounds B and C are the isomers Silybin (Silymarin I) and Silychristin (Silymarin III), respectively. It is useful to carry out the heating under nitrogen, as otherwise there is the risk of formation of dehydro compounds of the original polyhydroxyphenylchromanones. An appropriate illustrative solvent for the extraction of the filtrate is ethyl acetate and suitable solvents for the fractional crystallization are, e.g., methanol, ethanol and isopropanol.

Taking Silybin as an example, the preparative method of the invention is set forth in the following reaction pattern:

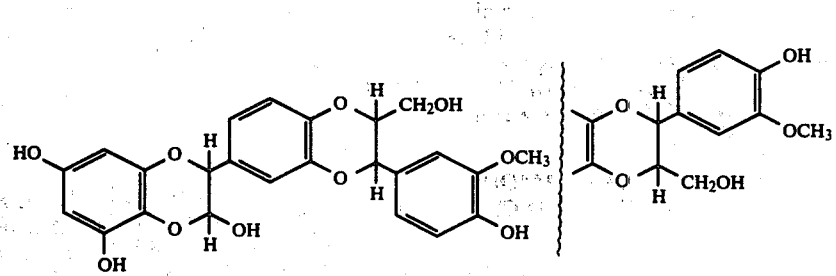

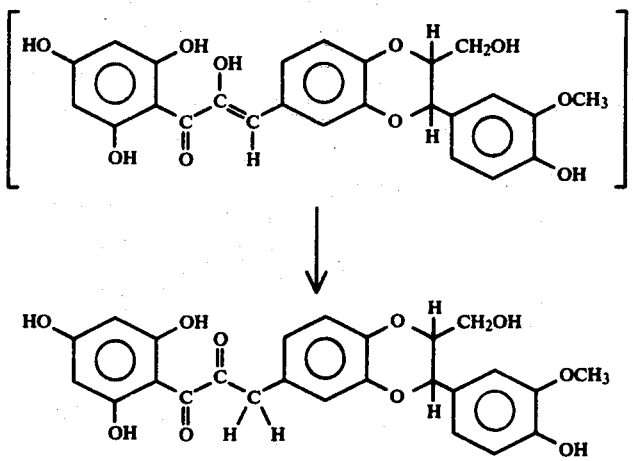

The pH-conditions in this process are adjusted to prevent the formation of an α-hydroxy acid by benzilic acid rearrangement. The selected pH-values and other conditions prevent the splitting of the compounds obtained into phloroglucinol and a substituted benzoic acid, or further splitting of same.

The compounds according to the invention can also be prepared as follows:

The aforementioned coniferylalcohol substituted with polyhydroxyphenylchromanone-3-ols is heated above its melting point and the melt is kept at this temperature for several hours, (e.g., from 2–4 hours), is then cooled down to room temperature, and then pulverized. Subsequently, a fractional crystallization of the compound obtained is performed to free it from unreacted starting materials.

The following examples are illustrative but not limitative of the preparation of the compounds of the invention.

EXAMPLE 1 FOR COMPOUND B (OR COMPOUND C)

4.2 g Silymarin I (Silybin), or Silymarin III (Silychristin) together with 1.95 g N-methyl glucamine salt were heated in water for 6 hours. Subsequently, the solution, cooled down to room temperature, was acidified with hydrochloric acid, the precipitate was centrifuged or filtered off and the filtrate was extracted with ethyl acetate. After distilling off the ethyl acetate under reduced pressure, the residue was added to the previously separated precipitate. The product can be freed from non-converted Silymarin I (or Silymarin III) by fractional crystallization from methanol. The yield for Compound B from Silymarin I (Silybin) was 3.52 g (73% of the theory); the melting point lies at 158°–162°. The yield for Compound C from Silymarin III (Silychristin) was 3.41 g (70.72% of the theory); the melting point lies at 204°–205°.

EXAMPLE 2 FOR COMPOUND B (OR COMPOUND C)

9.65 g of Silymarin I (Silybin) or Silymarin III (Silychristin) was suspended in a solution of 10 g NaHCO$_3$ in 200 ml water and the suspension was heated for 6 hours gradually resulting in a clear solution. The cooled reaction mixture was subsequently acidified with hydrochloric acid and further treated as in Example 1. The yield for Compound B from Silymarin I (silybin) was 4 g (42% of the theory. The yield for compound C from Silymarin III (Silychristin) was 3.71 g (39.0% of the theory).

EXAMPLE 3 FOR COMPOUND B (OR FOR COMPOUND C)

4.82 g of Silymarin I (Silybin) or Silymarin III (Silychristin) was heated up to 185° and the melt was left at this temperature for 3 hours. After cooling down to room temperature, the material was pulverized and fractionally crystallized from methanol, in which case any Silymarin I not opened to the α-diketone crystallizes out first. The yield for Compound B from Silymarin I (Silybin) is 2.7 g (57% of the theory). The yield for Compound C from Silymarin III (Silychristin) was 2.61 g (55.07% of the theory).

Figure 2:
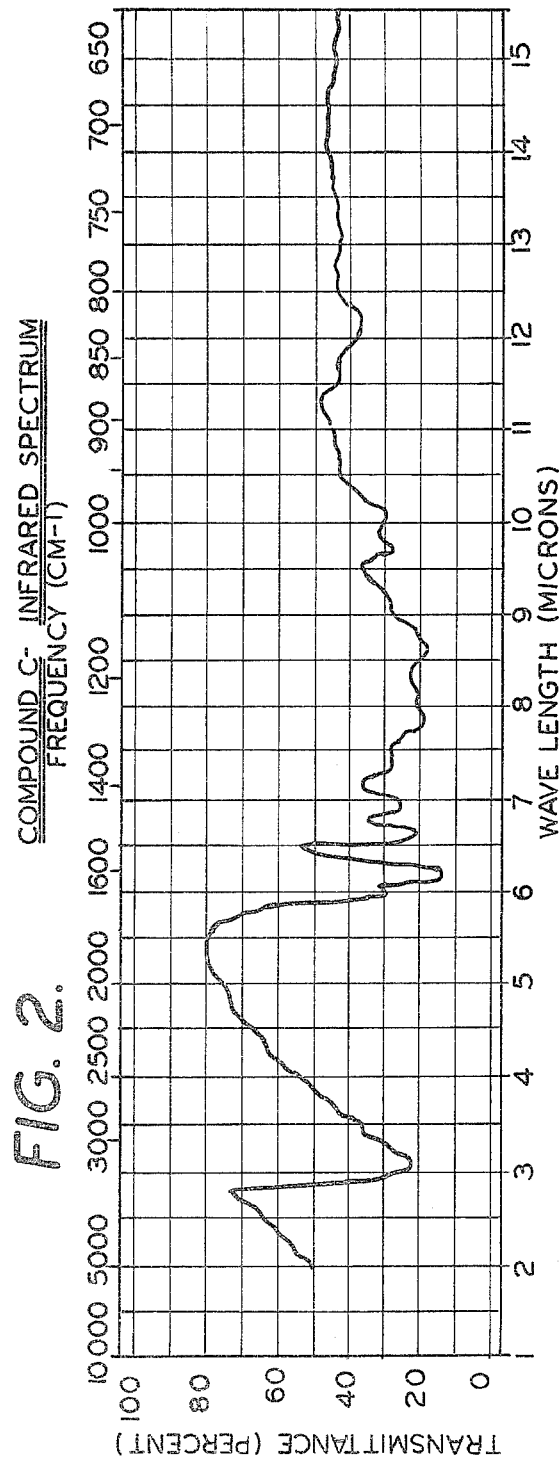
Figure 3:
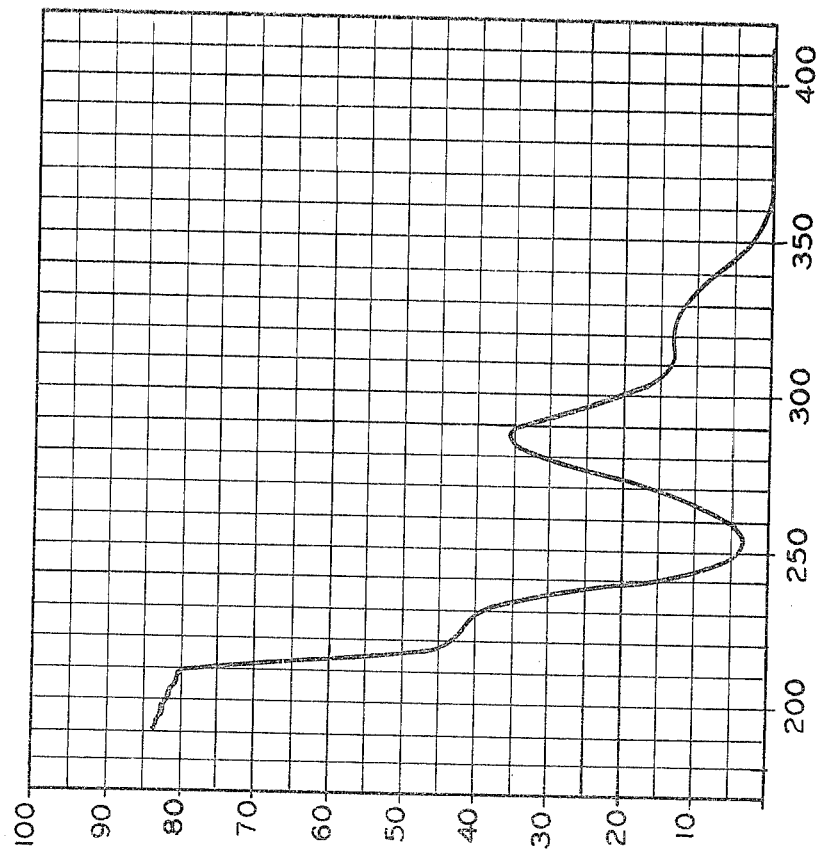
Figure 4:
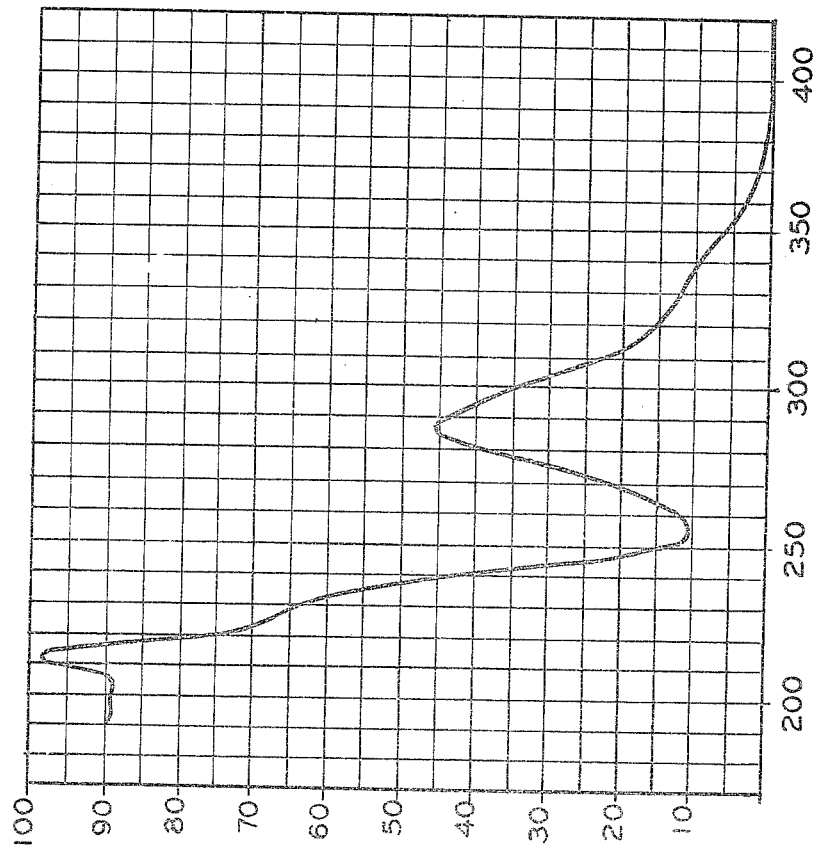

The I.R. and U.V. spectra of compounds B and C are set forth in FIGS. 1–4 of the accompanying drawings.

The substituted 1-(2',4',6'-trihydroxyphenyl)-propanedione (1,2)-compounds of the general formula A according to the invention can be converted, in the usual manner, to their physiologically compatible salts. Agents suitable for the salt formation are for example weakly basic amines such as triethanolamine, trimethylamine, triethylamine, amino sugar, etc.

The compounds of the general formula A of the invention as well as their salts are distinguished by their valuable therapeutic qualities. They show a particularly strong, protective and stabilizing effect on the cellular and intracellular biomembranes as locations of the cytometabolism, in particular on the cells of the liver, i.e., a strong liver-protective effect, and hence can be used for example in the treatment of liver diseases.

The following experiments illustrate the pharmacological activity of these compounds.

EXPERIMENT A

The acute toxicity of the compounds of the invention was tested on mice, and since the substances are substantially nontoxic after oral administration, the acute tolerance of the two Compounds B and C in their methyl glucamine salts form was determined after i.v. injection. This form of preparation was also chosen for the pharmacological measurement of the antiphalloidine effect.

Experimental animals were male and female SPF-mice, stock NMRI, of the firm of Voss, Tuttlingen, Germany, having a weight of about 25–30 g. each. All animals were housed under identical conditions and were given "Sniff" standard food and drinking water ad libitum. The mice were administered the dosages once in 20 ml 0.9% NaCl+4% PVP/kg i.v. at an injection rate of approximately 1 ml/min. The observation time was 14 days.

Substances and Solutions

1. Compound B as N-methyl glucamine salt.
2. Compound C as N-methyl glucamine salt.
3. Polyvinyl pyrrolidone (PVP) of Fluka, mol. wt. ~10,000 stock solution: 4% PVP dissolved in 0.9% NaCl.

The results are set forth in Table 1, below:

Table 1

Compound B
(a) male mice

| dosage mg/kg i.v. | No. | death rate/No. | death rate % | survival time span (minutes–hours) | death rate/day 1st | 2nd | 3rd | 13th | 14th |
|---|---|---|---|---|---|---|---|---|---|
| 425 | 5 | 0/5 | 0 | — | — | — | — | — | — |
| 600 | 10 | 0/10 | 0 | — | — | — | — | — | — |
| 714.1 | 10 | 3/10 | 30 | $23'-72^h$ | 1 | — | 2 | — | — |
| 850 | 10 | 8/10 | 80 | $30'-23^h$ | 8 | — | — | — | — |
| 1200 | 5 | 5/5 | 100 | $12'-23^h$ | 5 | — | — | — | — |
| 1700 | 3 | 3/3 | 100 | $4-5'$ | 3 | — | — | — | — |

$DL_{50}$ for male mice: $820 \pm 34$ mg/kg of Compound B as its N-methyl glucamine salt i.v. which compounds to 583.63 mg/kg of Compound B.

(b) female mice

| dosage mg/kg i.v. | No. | death rate/No. | death rate % | survival time span minutes–hours | death rate/day 1st | 2nd | 3rd | 13th | 14th |
|---|---|---|---|---|---|---|---|---|---|
| 570 | 10 | 0/10 | 0 | — | — | — | — | — | — |
| 680 | 10 | 1/10 | 10 | $abt.23^h$ | 1 | — | — | — | — |
| 800 | 10 | 3/10 | 30 | $22'-23^h$ | 3 | — | — | — | — |
| 960 | 10 | 7/10 | 70 | $18'-23^h$ | 7 | — | — | — | — |

$DL_{50}$ for female mice: $850 \pm {}^{64}_{59}$ mg/kg of Compound B as its N-methyl glucamine salt i.v. which compounds to 604.98 mg/kg of Compound B.

Compound C
(a) male mice

| dosage mg/kg i.v. | No. | death rate/No. | death rate % | survival time span minutes–hours | death rate/day 1st | 2nd | 3rd | 4th | 13th | 14th |
|---|---|---|---|---|---|---|---|---|---|---|
| 300 | 10 | 0/10 | 0 | — | — | — | — | — | — | — |
| 424.3 | 10 | 4/10 | 40 | $40^h-72^h$ | — | 3 | 1 | — | — | — |
| 504.6 | 5 | 5/5 | 100 | $20'-20^h$ | 5 | — | — | — | — | — |
| 600 | 5 | 5/5 | 100 | $2'-29'$ | 5 | — | — | — | — | — |

$DL_{50}$ for male mice: $415 \pm {}^{14.8}_{14.5}$ mg/kg of Compound C as its N-methyl glucamine salt i.v. which compounds to 295.34 mg/kg of Compound C.

(b) female mice

| dosage mg/kg i.v. | No. | death rate/No. | death rate % | survival time span minutes–hours | death rate/day 1st | 2nd | 3rd | 4th | 13th | 14th |
|---|---|---|---|---|---|---|---|---|---|---|
| 300 | 10 | 0/10 | 0 | — | — | — | — | — | — | — |
| 424.3 | 10 | 8/10 | 80 | $20^h-92^h$ | — | 1 | 5 | 2 | — | — |
| 504.6 | 5 | 5/5 | 100 | $27'-20^h$ | 5 | — | — | — | — | — |
| 600 | 5 | 5/5 | 100 | $2'-8'$ | 5 | — | — | — | — | — |

$DL_{50}$ for female mice: $385 \pm {}^{16.9}_{16.1}$ mg/kg of Compound C as its N-methyl glucamine salt i.v. which compounds to 274.02 mg/kg of Compound C.

Evaluation

The acute symptoms of non-tolerance are fairly similar for Compounds B and C: accelerated respiration, laying on their side, and clonic tonic cramps before death actually occurred.

EXPERIMENT B

The liver-protective effect of the compounds B and C according to the invention in the form of their water-soluble N-methyl glucamine salts was tested on mice by antagonizing liver damage induced by phalloidine with treatment using the compounds of the invention.

Substances and solutions

1.
Compound B as N-methyl glucamine salt
140.5 mg of Compound B/25 ml 0.9% NaCl+4% PVP/kg i.v.
=100 mg/kg of Compound B

2.

N-methyl glucamine salt (MG)
40.5 mg MG/25 ml 0.9% NaCl+4% PVP/ig i.v.
40.5 mg is the MG portion of 140.5 mg of Compound B

3.

Polyvinyl pyrrolidone (PVP) of Fluka, mol. wt. ~ 10,000
stock solution: 4% PVP dissolved in 0.9% NaCl.

4.
Phalloidine, predissolved in 3 ml methanol to 20 ml 0.9%
NaCl/ig i.p.

Method

Experimental animals were male and female mice of a homebred strain, stock Garvens, having a weight of about 20–25 g. All animals were housed under identical conditions and were given "Ssniff" standard food and drinking water ad libitum.

Compound B as its N-methyl glucamine salt was injected in a dosage of 140.5 mg/kg i.v. 1 hour prior to administration of phalloidine at 3 mg/kg i.p. (to induce damage to the liver). The control animals received 40.5 mg/kg N-methyl glucamine salt i.v. The death rate and survival time after the phalloidine poisoning were registered. The observation time was 7 days.

The results are set forth in Table 2, below

Table 2

Test on anti-phalloidine effect on male and female mice

Treatment:
140.5 mg/kg of Compound B as its N-methyl glucamine
salt i.v. or 40.5 mg/kg N-methyl glucamine salt i.v. 1 hour before
phalloidine poisoning (3 mg/kg i.p.).

| Experimental animal group | No. | death rate % | survival time min. |
|---|---|---|---|
| Control animals | 20 | 80 | 164.8 ± 6.8 |
| Experimental animals | 20 | 0 | — |

The substantially lethal phalloidine poisoning (DL$_{80}$) measured by the death rate and survival time is prevented by a treatment with Compound B as its N-methyl glucamine salt.

EXPERIMENT C

As an additional pharmacological measurement, the antiphalloidine effect of Compound C as its N-methyl glucamine salt i.v. was subsequently determined.

Substances and solutions

1.
Compound C as N-methyl glucamine salt
140.5 mg/20 ml 0.9% NaCl+4% PVP/kg i.v.
= 100 mg/kg of Compound C 2.
N-methyl glucamine salt (MG)
40.5 mg/20 ml 0.9% NaCl+4% PVP/kg i.v.

3.
Polyvinyl pyrrolidone (PVP) of Fluka, mol. wt. ~ 10,000
stock solutions: 4% PVP dissolved in 0.9% NaCl 4.
Phalloidine
1.5 mg phalloidine, predissolved in 3 ml methanol ad 20 ml
0.9 % NaCl/kg i.p.

5. GOT } monotest of Boehringer-Mannheim GmbH, Germany
   GPT

Method

Experimental animals were female SPF-mice, stock NMRI, of the firm of Voss, Tuttlingen, having a weight of about 25 g. All animals were housed under identical conditions and were given "Ssniff" standard food and drinking water ad libitum. Compound C as its N-methyl glucamine salt was injected in a dosage of 140.5 mg/kg i.v. 1 hour before the phalloidine poisoning (1.5 mg/kg i.p.). The control animals received 40.5 mg/kg N-methyl glucamine salt i.v. after a period of 24 hours subsequent to the damage to the liver, blood was taken from the mice from the retroorbital venae plexus for the determination of the serum enzymes GOT and GPT.

The results are set forth on Table 3, below.

Table 3

Test on anti-phalloidine effect on female mice treatment: 140.5 mg/kg of Compound C as its N-methyl glucamine
salt i.v. or 40.5 mg/kg MG (N-methyl glucamine salt) i.v.
1 hour before the phalloidine-induced damage to the liver 1.5 mg/
kg i.p.). 24 hours after the phalloidine poisoning: determination
of GOT and GPT in the serum.

| Experimental animal group | no. | GOT mU/ml | GPT mU/ml |
|---|---|---|---|
| Control animals | 10 | 1489.2±904.7 | 667.4±324.6 |
| Experimental animals | 10 | 38.7±2.9 | 13.4±0.9 |

The phallodine-induced, serious damage to the liver, measured by the increase of the serum enzymes GOT (glutamate oxalacetate transaminase) and GPT (glutamate pyruvate transaminase), was entirely prevented by a treatment with Compound C as its N-methyl glucamine salt i.v.

The compounds and salts of the invention can be used orally, enterally or parenterally. The dosage depends on the seriousness of the illness, weight and condition of the patient as well as duration and intensity of the treatment. For example, 50 to 300 mg/day can be administered orally. The water-soluble salts can be injected in daily dosages of about 30 to 300 mg/day in the form of injection preparations, and can be administered as an additive or infusion. Both the compounds and salts of the invention are well-tolerated by mammals.

The inventive compounds or their salts can also be used along with other preventives for liver disorders, or with other active substances, e.g., as choleretica, antiphlogistica, spasmolytica, digestive aids and enzymes, kipotropes or the like. Appropriate galenic forms of administration are, e.g., tablets, dragees, capsules, lozenges, solutions or powders; the usual galenic auxiliary carriers, disintegrating or lubricating agents or substances to obtain a depositing effect can be used in their preparation. Such galenic forms are produced in the usual manner according to the known methods of preparation.

Galenic example: tablets 35 kg of the compound according to the invention are mixed with the following auxiliary materials:

| | |
|---|---|
| 5.000 kg | polyvinyl pyrrolidone |
| 7.200 kg | microcrystalline cellulose |
| 8.700 kg | amylum tritici |
| 3.250 kg | aerosil |
| 5.000 kg | stearic acid |
| 185.850 kg | lactose DIN 80 |

Tablets of 0.25 g (containing 35 mg of active material) are subsequently pressed.

Galenic example: ampules

For the preparation of 10,000 ampules, 0.315 kg of N-methyl glucamine salt of the compound according to the invention is dissolved in 49.685 liters of physiological salt solution, to which 4% polyvinyl pyrrolidone (mol.wt. ~ 10,000) was added. The pH-value should not be below 7.6. The solution undergoes sterilized filtration and is brought into sterilized brown 5-ml ampules, so that the content per ampule amounts to 31.5 mg of N-methyl glucamine salt.

It will be understood that the specification and examples are illustrative but not limitative of the present invention and that other embodiments within the spirit and scope of the invention will suggest themselves to those skilled in the art.

What is claimed is:

1. 1-(2',4',6'-Trihydroxyphenyl)-propanedione-(1,2)-compound of the formula

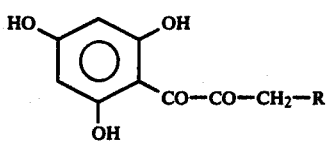

wherein
R is a coniferyl alcohol-containing group selected from

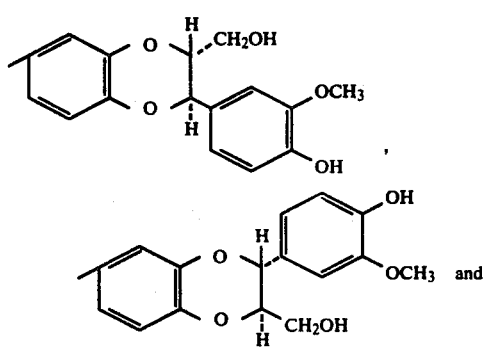

2. 1-(2',4',6'-Trihydroxyphenyl)-propanedione-(1,2)-compound as claimed in claim 1 of the formula

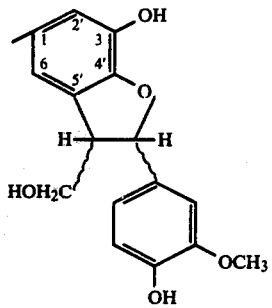

3. 1-(2',4',6'-Trihydroxyphenyl)-propanedione-(1,2)-compound as claimed in claim 1 of the formula

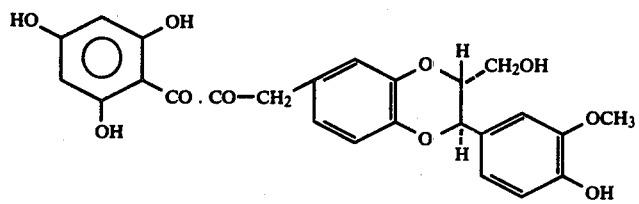

4. 1-(2',4',6'-Trihydroxyphenyl)-propanedione-(1,2)-compound as claimed in claim 1 of the formula

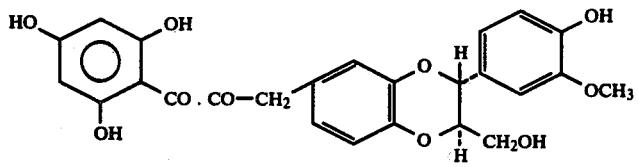

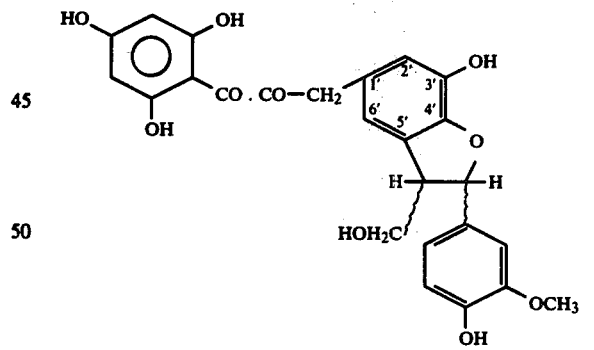

5. Process for the preparation of a 1-(2',4',6'-trihydroxyphenyl)-propanedione-(1,2)-compound as claimed in claim 1 which process comprises treating coniferylalcohol substituted with the corresponding polyhydroxyphenylchromanone-3-ol in alkaline medium at a pH value of from about 7.3 to 7.8 heating the resulting mixture from 4 to 6 hours, acidifying the said mixture, drying the resulting precipitate, extracting the filtrate, distilling off the solvent under reduced pressure and separating the resulting desired product by fractional crystallization.

6. Process claimed in claim 5 wherein said heating takes place under a nitrogen atmosphere.

7. Process claimed in claim 5 wherein said substituted coniferylalcohol is heated above its melting point during said heating step and the melt is kept at such temperature for several hours, the resulting mixture is cooled to room temperature, the resulting solid material is pulverized and the pulverized mixture is subjected to fractional crystallization to free the desired product from unconverted reactants.

8. Therapeutic composition for the treatment of liver diseases comprising a pharmaceutically acceptable carrier and an effective amount, of a 1-(2',4',6'-trihydroxyphenyl)-propanedione-(1,2)-compound as claimed in claim 1.

9. Method of treating a subject having a liver disease which method comprises administering to such subject an effective amount of a 1-(2',4',6'-trihydroxyphenyl)-propane-dione-(1,2)-compound as claimed in claim 1.

* * * * *